US012733856B2

(12) United States Patent
Saito et al.

(10) Patent No.: US 12,733,856 B2
(45) Date of Patent: Sep. 15, 2026

(54) OPTICALLY PUMPED MAGNETOMETER AND MAGNETOENCEPHALOGRAPH

(71) Applicants: HAMAMATSU PHOTONICS K.K., Hamamatsu (JP); Kyoto University, Kyoto (JP)

(72) Inventors: Akinori Saito, Hamamatsu (JP); Takenori Oida, Hamamatsu (JP); Takahiro Moriya, Hamamatsu (JP); Motohiro Suyama, Hamamatsu (JP); Yosuke Ito, Kyoto (JP); Hiroyuki Ueda, Kyoto (JP)

(73) Assignees: HAMAMATSU PHOTONICS K.K., Hamamatsu (JP); Kyoto University, Kyoto (JP)

( * ) Notice: Subject to any disclaimer, the term of this patent is extended or adjusted under 35 U.S.C. 154(b) by 169 days.

(21) Appl. No.: 18/765,392

(22) Filed: Jul. 8, 2024

(65) Prior Publication Data

US 2025/0072803 A1 Mar. 6, 2025

(30) Foreign Application Priority Data

Aug. 31, 2023 (JP) ................................ 2023-141422

(51) Int. Cl.
*A61B 5/245* (2021.01)
*G01R 33/26* (2006.01)

(52) U.S. Cl.
CPC .............. *A61B 5/245* (2021.01); *G01R 33/26* (2013.01); *A61B 2562/0223* (2013.01)

(58) Field of Classification Search
None
See application file for complete search history.

(56) References Cited

U.S. PATENT DOCUMENTS

| | | | | |
|---|---|---|---|---|
| 8,427,146 | B2 * | 4/2013 | Nagasaka | G01R 33/26 324/304 |
| 9,726,733 | B2 * | 8/2017 | Smith | G01R 33/26 |
| 9,869,371 | B2 * | 1/2018 | Flemming | F16D 28/00 |

(Continued)

OTHER PUBLICATIONS

Limes, M. E. et al., "Portable magnetometry for detection of biomagnetism in ambient environments," Jun. 2, 2020, pp. 1-10.

(Continued)

*Primary Examiner* — Richard Isla
(74) *Attorney, Agent, or Firm* — Faegre Drinker Biddle & Reath LLP

(57) ABSTRACT

An optically pumped magnetometer includes a cell, a pump light incidence unit causing pump light to be incident on a plurality of sensitivity regions inside the cell in a first direction, a probe light incidence unit causing probe light to be incident on the sensitivity regions in a direction intersecting the first direction, bias magnetic field coils applying a bias magnetic field to the inside of the cell and determining a resonance frequency of the electron spins, an electron spin tilting unit tilting a rotation axis direction of the electron spins in a direction perpendicular to the first direction, an optical sensor detecting the probe light; and a magnetic field measuring unit measuring magnetic field strengths related to the sensitivity regions, wherein the bias magnetic field coils respectively apply a plurality of the bias magnetic fields having strengths different from each other to the plurality of corresponding sensitivity regions.

8 Claims, 12 Drawing Sheets

(56) References Cited

U.S. PATENT DOCUMENTS

| | | | | |
|---|---|---|---|---|
| 10,782,368 | B2 | 9/2020 | Bulatowicz et al. | |
| 11,555,872 | B2 * | 1/2023 | Romero | G01R 33/091 |
| 12,174,020 | B2 * | 12/2024 | Lee | G01C 17/28 |
| 2022/0091200 | A1 | 3/2022 | Gerginov | |
| 2025/0076423 | A1 * | 3/2025 | Moriya | G01N 24/006 |

OTHER PUBLICATIONS

Lucivero, V. G. et al., "Femtotesla nearly quantum-noise-limited pulsed gradiometer at Earth-scale fields," Dec. 17, 2021, pp. 1-5.

* cited by examiner y
z
5
4
35
21
36
22
6
8
43a
44a
45a
49
48
24a
23b
24b
23c
25
38
23a
7
9
27a
27b
27c
27d
47
PLa
PLb
PLc
PLd
QL
46
Rf
37a
ARa
ARb
ARc
ARd
2
Bm
Bm 16a(15)
15a(15)
15b(15)
15c(15)
15d(15)
16b(15)
2
2
17
x
y
z 16a(15)
15a(15)
15b(15)
15c(15)
15d(15)
16b(15)
2
17
17
x
y
z 1A
x
y
z
4
21
22
29
By
7
5
35
36
38
10
43a
43b
48
49
9
46
47
Rf
2
37a
37b
37c
6
23a
23b
23c
24a
24b
25
27a
27b
27c
27d
115a(115)
115b(115)
115c(115)
115d(115)

OPTICALLY PUMPED MAGNETOMETER AND MAGNETOENCEPHALOGRAPH

TECHNICAL FIELD

The present disclosure relates to an optically pumped magnetometer and a magnetoencephalograph including the same.

BACKGROUND

An optically pumped magnetometer capable of measuring a weak external magnetic field is known (for example, refer to United States Patent Application Publication No. 2022/0091200 and U.S. Pat. No. 10,782,368). In the optically pumped magnetometer, alkali metal atoms inside a cell are pumped by pump light, probe light radiated toward the cell in a manner of intersecting the pump light is measured by an optical sensor, and a strength of an external magnetic field is detected based on an output of the optical sensor.

SUMMARY

In such optically pumped magnetometers described above, it is sometimes desired to perform multi-channel measurement of magnetic field strengths. However, in this case, the constitution of an optical system is likely to be complicated. Hence, the present disclosure aims to provide an optically pumped magnetometer and a magnetoencephalograph enabling multi-channel measurement of magnetic field strengths with a simple constitution.

An optically pumped magnetometer according to an aspect of the present disclosure may be, [1] "an optically pumped magnetometer including a cell configured to be filled with alkali metal vapor, a pump light incidence unit configured to cause pump light for pumping alkali metal atoms constituting the alkali metal vapor to be incident on a plurality of sensitivity regions inside the cell in a first direction, a probe light incidence unit configured to cause probe light for detecting change in electron spins in a pumped state of the alkali metal atoms to be incident on the plurality of sensitivity regions in a direction intersecting the first direction, bias magnetic field coils configured to apply a bias magnetic field in the first direction to the inside of the cell and determine a resonance frequency of the electron spins, an electron spin tilting unit configured to tilt a rotation axis direction of the electron spins in a direction perpendicular to the first direction, an optical sensor configured to detect the probe light having passed through the sensitivity regions, and a magnetic field measuring unit configured to measure magnetic field strengths related to the sensitivity regions based on an output of the optical sensor, in which the bias magnetic field coils respectively apply a plurality of the bias magnetic fields having strengths different from each other to the plurality of corresponding sensitivity regions".

In this optically pumped magnetometer, the magnetic field strengths related to a plurality of sensitivity regions can be obtained using one ray of probe light by changing the strength of a bias magnetic field for each of the plurality of sensitivity regions. That is, multi-channel measurement of magnetic field strengths can be performed with a simple constitution.

The optically pumped magnetometer according to the aspect of the present disclosure may be, [2] "the optically pumped magnetometer according to the foregoing [1] in which the plurality of sensitivity regions include at least a first sensitivity region and a second sensitivity region, and the bias magnetic field coils include a first coil corresponding to the first sensitivity region and a second coil corresponding to the second sensitivity region". In this case, change in strength of a bias magnetic field for each of a plurality of sensitivity regions can be specifically realized.

The optically pumped magnetometer according to the aspect of the present disclosure may be, [3] "the optically pumped magnetometer according to the foregoing [2] further including a substrate configured to be provided with the first coil and the second coil, in which a passing hole allowing the pump light to pass therethrough is formed in the substrate". In this case, the bias magnetic field coils can be specifically mounted without disturbing incidence of pump light on the cell.

The optically pumped magnetometer according to the aspect of the present disclosure may be, [4] "the optically pumped magnetometer according to the foregoing [2] or [3] in which the first sensitivity region is present in an end portion of the cell, and the bias magnetic field coils include an extra-cell coil disposed away from the cell when viewed in the first direction and adjacent to the first coil". In this case, the strength on the end portion side of the cell in a bias magnetic field applied to the first sensitivity region can be appropriately maintained by the extra-cell coil.

The optically pumped magnetometer according to the aspect of the present disclosure may be, [5] "the optically pumped magnetometer according to the foregoing [1] in which the plurality of sensitivity regions include a first sensitivity region, a second sensitivity region adjacent to the first sensitivity region, a third sensitivity region adjacent to the second sensitivity region, and a fourth sensitivity region adjacent to the third sensitivity region; and the bias magnetic field coils include a pair of first coils disposed with the first sensitivity region sandwiched therebetween in the first direction and formed with a first number of windings in a first rotation direction, a pair of second coils disposed with the second sensitivity region sandwiched therebetween in the first direction and formed with a second number of windings in the first rotation direction, a pair of third coils disposed with the third sensitivity region sandwiched therebetween in the first direction and formed with the second number of windings in a second rotation direction opposite to the first rotation direction, and a pair of fourth coils disposed with the fourth sensitivity region sandwiched therebetween in the first direction and formed with the first number of windings in the second rotation direction". In this case, change in strength of a bias magnetic field for each of a plurality of sensitivity regions can be specifically realized.

The optically pumped magnetometer according to the aspect of the present disclosure may be, [6] "the optically pumped magnetometer according to any one of the foregoing [1] to [5] in which the plurality of sensitivity regions include first to Nth sensitivity regions (N is an integer equal to or larger than 2); the bias magnetic field coils respectively apply first to Nth bias magnetic fields to the first to Nth sensitivity regions and have first to Nth resonance frequencies as the resonance frequencies of the first to Nth sensitivity regions; and the magnetic field measuring unit acquires a mixed waveform of free induction decay including components of the first to Nth resonance frequencies based on an output of the optical sensor, filters the mixed waveform through a band pass filter, acquires first to Nth waveforms of free induction decay in respective bands of the first to Nth resonance frequencies, derives respective frequencies of the first to Nth waveforms, and obtains magnetic field strengths related to the first to Nth sensitivity regions on the basis of the respectively derived frequencies of the first to Nth waveforms". In this case, the magnetic field strengths related to the first to Nth sensitivity regions can be specifically measured.

The optically pumped magnetometer according to the aspect of the present disclosure may be, [7] "the optically pumped magnetometer according to any one of the foregoing [1] to [6] in which the electron spin tilting unit radiates RF signals having the same frequencies as the resonance frequencies". In this case, the rotation axis direction of electron spins can be tilted utilizing RF signals.

The optically pumped magnetometer according to the aspect of the present disclosure may be, [8] "the optically pumped magnetometer according to any one of the foregoing [1] to [6] in which the electron spin tilting unit radiates pulsed light". In this case, the rotation axis direction of electron spins can be tilted utilizing pulsed light.

The optically pumped magnetometer according to the aspect of the present disclosure may be, [9] "the optically pumped magnetometer according to any one of the foregoing [1] to [8] in which the magnetic field measuring unit measures the magnetic field strengths based on a difference between outputs of the optical sensor corresponding to the two adjacent sensitivity regions". In this case, common mode noise which is common to two sensitivity regions is removed so that measurement of a weak magnetic field strength can be realized.

A magnetoencephalograph according to another aspect of the present disclosure is, [10] "a magnetoencephalograph including the optically pumped magnetometer according to any one of the foregoing [1] to [9] configured to be provided in a manner of being able to be disposed around the head of a test object and measure a strength of a magnetic field emitted from the test object".

Since this magnetoencephalograph is also provided with the foregoing optically pumped magnetometer, the foregoing operational effect of enabling multi-channel measurement of magnetic field strengths with a simple constitution is exhibited.

BRIEF DESCRIPTION OF THE DRAWINGS

FIG. 3 is timing charts showing generation timings of pump light, an RF signal, and probe light during processing of measuring an external magnetic field by a read circuit in FIG. 1.

DETAILED DESCRIPTION

Hereinafter, an embodiment of the present disclosure will be described in detail with reference to the accompanying drawings. In description, the same reference signs are used for the same elements or elements having the same function, and duplicate description thereof will be omitted.

Figure 1:
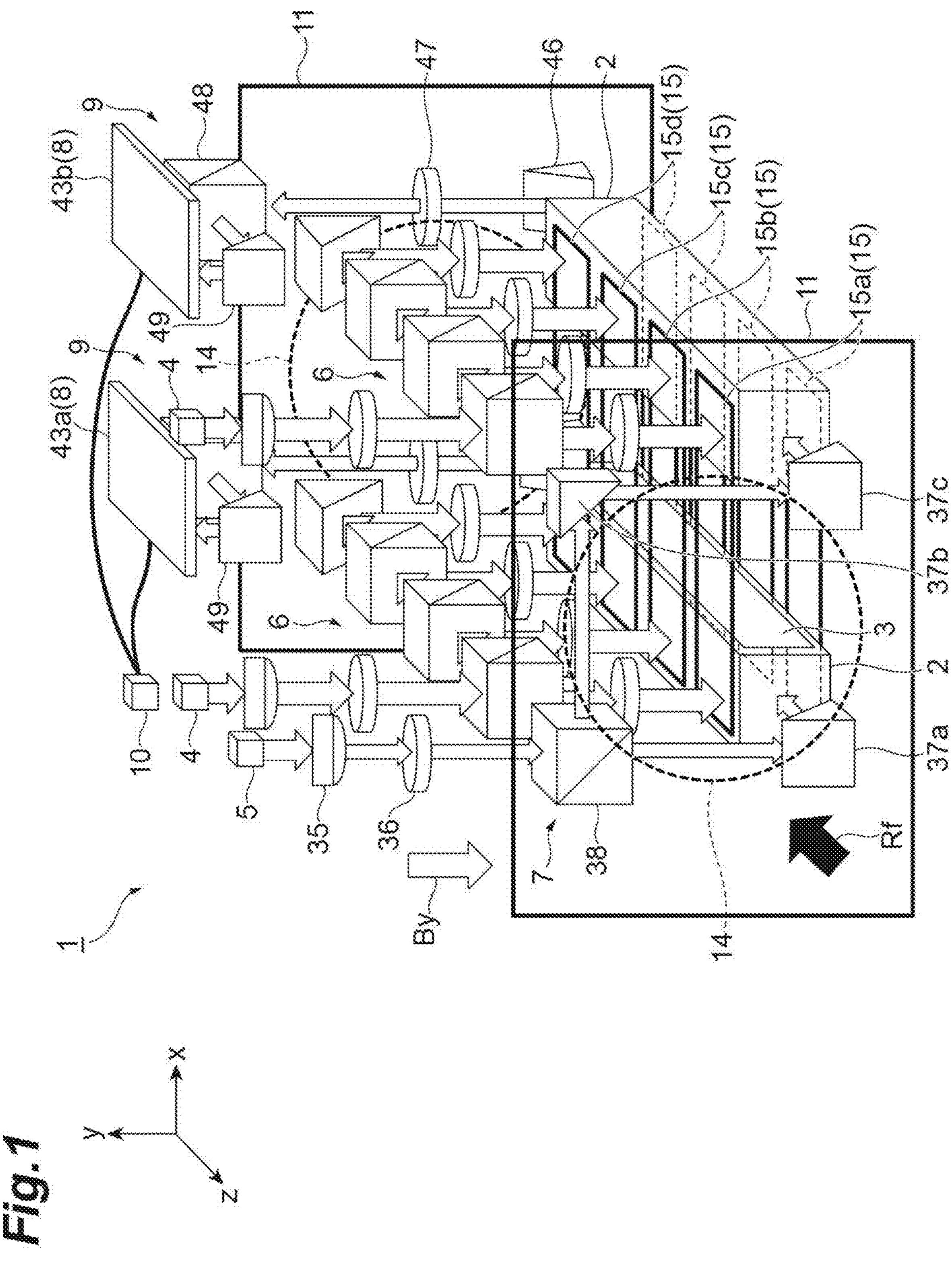
FIG. 1 is a perspective view illustrating a constitution of an optically pumped magnetometer according to an embodiment.

FIG. 1 is a perspective view illustrating a constitution of an optically pumped magnetometer 1 according to the embodiment. The optically pumped magnetometer 1 is a device for measuring an external magnetic field utilizing optical pumping. In the present embodiment, the optically pumped magnetometer 1 will be described as being used for magnetoencephalographic measurement, but the usage is not limited thereto. As an example, a measurement target of the optically pumped magnetometer 1 is a cerebral magnetic field. For the sake of description, in FIG. 1, a direction lying in a magnetic field direction of a measurement target is a y axis. Two axes perpendicular to the y axis, which are axes constituting a three-dimensional coordinate system together with the y axis and perpendicular to each other, are an x axis and a z axis, respectively. In the following description, a positive direction and a negative direction along the x axis will be respectively expressed as a positive x axis direction and a negative x axis direction, a positive direction and a negative direction along the y axis will be respectively expressed as a positive y axis direction and a negative y axis direction, and a positive direction and a negative direction along the z axis will be respectively expressed as a positive z axis direction and a negative z axis direction. The y axis direction corresponds to a first direction.

As illustrated in FIG. 1, the optically pumped magnetometer 1 includes cells 2, heaters 3, a pump laser 4, a probe laser 5, a first optical system 6, a second optical system 7, an optical sensor group 8, third optical systems 9, a read circuit 10, bias magnetic field coils 11 and 15, and a tilting coil (electron spin tilting unit) 14. The optically pumped magnetometer 1 is an axis-type sensor. Hereinafter, constitution elements of the optically pumped magnetometer 1 will be described in detail.

The cells 2 are containers to be filled with alkali metal vapor. The cells 2 are disposed in the z axis direction. Two cells 2 are provided side by side in the x axis direction. The cells 2 substantially have a rectangular parallelepiped bottomed tubular shape with a surface substantially parallel to an xz plane. Cross sections of the cells 2 in a direction perpendicular to a longitudinal direction of the cells 2 (a direction along an xy plane) have a square shape, for example. The cells 2 may be constituted using a material such as quartz, sapphire, silicon, Kovar glass, or borosilicate glass, for example. The cells 2 allow light transmission with respect to pump light and probe light, which will be described below. The heaters 3 and the like are attached to side surfaces of the two cells 2 facing each other. A magnetic field Bm of a measurement target generated from the measurement target is incident in the positive y axis direction on the side surfaces of the cells 2 in the negative y axis direction.

An alkali metal constituting alkali metal vapor filling the cells 2 may be, for example, at least one or more kinds from lithium (Li), sodium (Na), potassium (K), rubidium (Rb), and cesium (Cs). For example, the alkali metal may be potassium and rubidium or may simply be potassium. Potassium has a comparatively low spin-destruction collision relaxation rate among the kinds of alkali metal used in an optically pumped magnetometer. For example, the spin-destruction collision relaxation rate of potassium is lower than those of cesium, rubidium, and the like. Therefore, when a single alkali metal is employed, an optically pumped magnetometer simply using potassium has a higher sensitivity than an optically pumped magnetometer simply using cesium or simply using rubidium.

In addition, the cells 2 accommodate a filler gas. The filler gas curbs relaxation of spin polarization of alkali metal vapor. In addition, the filler gas protects alkali metal vapor and curbs noise light emission. For example, the filler gas may be an inert gas such as helium (He), neon (Ne), argon (Ar), krypton (Kr), xenon (Xe), or nitrogen (N2). For example, the filler gas may be helium and nitrogen.

As described above, the heaters 3 are attached to the cells 2. The heaters 3 generate heat in response to a current supplied from a heater power source (not illustrated). The heaters 3 control the vapor density of alkali metal by controlling internal temperatures of the cells 2. For example, when potassium is accommodated in the cells 2 as an alkali metal, the heaters 3 heat the cells 2 such that the internal temperatures thereof become 120° C.

The pump laser 4 emits pump light for pumping alkali metal atoms in the negative y axis direction. That is, the pump laser 4 emits pump light (linear polarized light) and converts it into circularly polarized light through ¼ wavelength plates 27*a* to 27*d*. The alkali metal atoms accommodated in the cells 2 are pumped by pump light in a polarized state (circularly polarized light), and spin polarization occurs. The wavelength of pump light is set depending on the kind of atoms constituting alkali metal vapor (more specifically, the wavelength of an absorption line). For example, when atoms constituting alkali metal vapor are potassium, the wavelength of pump light is set to 770.11 nm matching the resonance line of potassium. When the alkali metal atoms accommodated in the cells 2 are potassium and rubidium, the pump laser 4 may emit pump light for transferring spin polarization of atoms of the rubidium to atoms of the potassium by pumping atoms of the rubidium. In this case, atoms of the rubidium are in a pumped state by the pump light. Further, spin polarization of atoms of the rubidium is transferred to atoms of the potassium due to spin exchange interaction between the potassium and the rubidium, and thus atoms of the potassium are in a pumped state.

Figure 2:
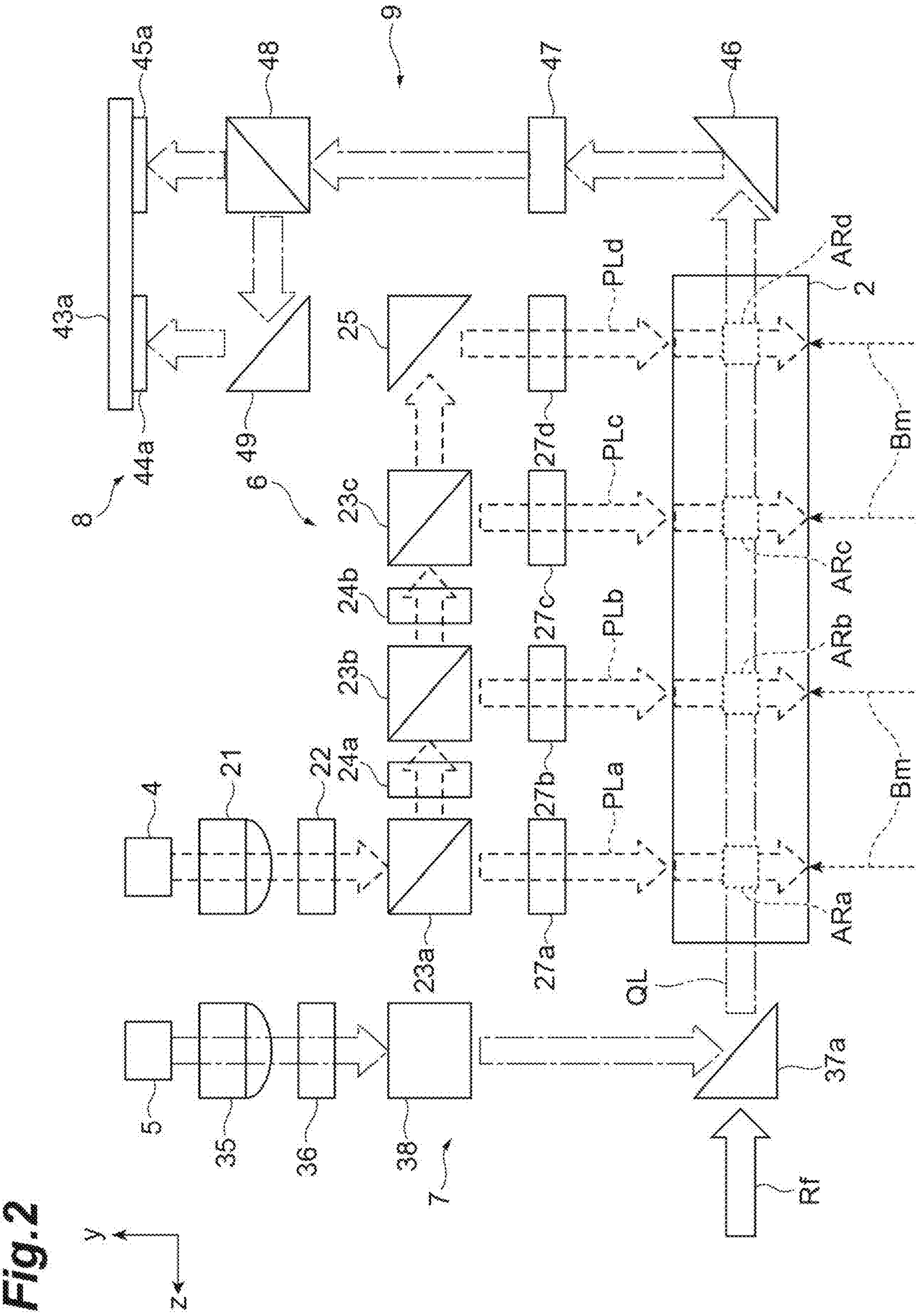
FIG. 2 is a plan view of a first optical system and a second optical system in FIG. 1 viewed in a negative x axis direction.

Pump light from the pump laser 4 is incident on the cells 2 via the first optical system 6. As illustrated in FIGS. 1 and 2, the first optical system 6 is constituted to include a lens 21, a ½ wavelength plate 22, polarization beam splitters 23*a*, 23*b*, and 23*c*, ½ wavelength plates 24*a* and 24*b*, a total reflection mirror 25, and the ¼ wavelength plates 27*a*, 27*b*, 27*c*, and 27*d*.

The lens 21 is provided adjacent to the pump laser 4 in the negative y axis direction and condenses pump light emitted from the pump laser 4. The ½ wavelength plate 22 is provided adjacent to the lens 21 in the negative y axis direction and rotates a polarization plane such that power of the pump laser 4 is distributed by 1:3 through the polarization beam splitter 23*a*.

The polarization beam splitter 23*a* is provided adjacent to the ½ wavelength plate 22 in the negative y axis direction and separates components of two rays of linear polarized light perpendicular to each other from a polarization component of pump light which has been transmitted through the ½ wavelength plate 22. The component of one ray of linear polarized light is transmitted therethrough in the negative y axis direction, and the component of the other ray of linear polarized light is reflected in the negative z axis direction. The polarization beam splitters 23*b* and 23*c* and the total reflection mirror 25 are provided side by side in order in the negative z axis direction with respect to the polarization beam splitter 23*a*. Each of the polarization beam splitters 23*b* and 23*c* separates the components of two rays of linear polarized light perpendicular to each other from pump light which has been transmitted through the polarization beam splitters 23*a* and 23*b*. The component of one ray of linear polarized light is transmitted therethrough in the negative z axis direction, and the component of the other ray of linear polarized light is reflected in the negative y axis direction. The total reflection mirror 25 reflects pump light (linear polarized light) which has been transmitted through the polarization beam splitter 23*c* in the negative y axis direction.

The ½ wavelength plate 24*a* is provided between the polarization beam splitter 23*a* and the polarization beam splitter 23*b* and rotates the polarization plane of pump light (linear polarized light) reflected by the polarization beam splitter 23*a*. Accordingly, the pump light can be separated into polarization components of two rays of linear polarized light by the polarization beam splitter 23*b*. The ½ wavelength plate 24*b* is provided between the polarization beam splitter 23*b* and the polarization beam splitter 23*c* and rotates the polarization plane of pump light (linear polarized light) which has been transmitted through the polarization beam splitter 23*b*. Accordingly, pump light can be separated into polarization components of two rays of linear polarized light by the polarization beam splitter 23*c*.

The ¼ wavelength plate 27*a* is provided adjacent to the polarization beam splitter 23*a* in the negative y axis direction. The ¼ wavelength plate 27*a* changes the polarized state of the pump light which has been transmitted through a polarizer 26*a* to that of circularly polarized light and allows it to be transmitted therethrough in the negative y axis direction as pump light PLa. The ¼ wavelength plates 27*b*, 27*c*, and 27*d* are provided respectively adjacent to the polarization beam splitters 23*b* and 23*c* and the total reflection mirror 25 in the negative y axis direction. Each of the ¼ wavelength plates 27*b*, 27*c*, and 27*d* has the same function as the ¼ wavelength plate 27*a* and allows rays of pump light PLb, PLc, and PLd to be transmitted therethrough in the negative y axis direction.

The first optical system 6 having the foregoing constitution is constituted such that rays of the pump light PLa to PLd of four systems transmitted through the four ¼ wavelength plates 27*a*, 27*b*, 27*c*, and 27*d* can be respectively incident on sensitivity regions ARa to ARd inside the cells 2. The pump laser 4 and the first optical system 6 constitute a pump light incidence unit causing rays of the pump light PLa to PLd to be incident on the sensitivity regions ARa to ARd in the negative y axis direction.

The probe laser 5 emits probe light for detecting precession of spins when electron spins in a pumped state of alkali metal atoms are laid 90 degrees. That is, the probe laser 5 emits probe light (linear polarized light). When passing through alkali metal vapor, probe light is influenced by the state of spin polarization of alkali metal atoms so that the polarization angle changes. The state of precession of spins can be derived upon detection of this change in polarization angle. The wavelength of probe light is set depending on the kind of atoms constituting alkali metal vapor (more specifically, the wavelength of an absorption line). For example, when simply potassium is accommodated in the cells 2 as an alkali metal, the wavelength of probe light is detuned from the wavelength of pump light (for example, 770.11 nm). For example, it is approximately 770.05 nm. Since the wavelength of probe light is detuned from the wavelength of pump light, absorption of probe light by potassium is curbed.

When potassium and rubidium are accommodated in the cells 2 as alkali metals, the probe laser 5 may emit probe light for detecting change in polarization angle caused by spin polarization in a pumped state of atoms of potassium. The density of rubidium used for pumping is set to be smaller than the density of potassium used for probing. When the density of rubidium is smaller than the density of potassium, decay of pump light due to pumping is curbed. Accordingly, the optically pumped magnetometer I can achieve a uniform sensitivity inside the cells 2.

Probe light from the probe laser 5 is incident on the cells 2 via the second optical system 7. The second optical system 7 is constituted to include a lens 35, a ½ wavelength plate 36, a polarization beam splitter 38, and total reflection mirrors 37*a* to 37*c*. The polarization beam splitter 38 is provided adjacent to the ½ wavelength plate 36 in the negative y axis direction and separates the components of two rays of linear polarized light perpendicular to each other from a polarization component of probe light which has been transmitted through the ½ wavelength plate 36. The component of one ray of linear polarized light is transmitted therethrough in the negative y axis direction, and the component of the other ray of linear polarized light is reflected in the positive x axis direction. The total reflection mirror 37*a* reflects the component of linear polarized light of probe light which has been transmitted through the polarization beam splitter 38 in the negative z axis direction and causes it to be incident on the inside of one cell 2 in the longitudinal direction thereof. The total reflection mirrors 37*b* and 37*c* continuously reflect the component of linear polarized light of probe light reflected by the polarization beam splitter 38 in the negative y axis direction and the negative z axis direction and cause it to be incident on the other cell 2 in the longitudinal direction thereof. The second optical system 7 having such a constitution is constituted such that rays of probe light QL of two systems can be respectively incident on the four sensitivity regions ARa to ARd arranged in the longitudinal direction (z axis direction) inside the cells 2 and intersecting pump light.

The sensitivity regions ARa to ARd are regions arranged away from each other in the longitudinal direction inside the cells 2. The sensitivity regions ARa to ARd are regions intersecting rays of the pump light PLa to PLd inside the cells 2. The sensitivity regions ARa to ARd are intersection regions where rays of the probe light QL and rays of the pump light PLa to PLd intersect each other. The probe laser 5 and the second optical system 7 constitute a probe light incidence unit causing rays of the probe light QL to be incident on the sensitivity regions ARa to ARd in the x axis direction.

The bias magnetic field coils 11 and 15 are coils applying bias magnetic fields By to the insides of the cells 2 in the y axis direction and determining resonance frequencies of electron spins of alkali metal atoms pumped inside the cells 2. The bias magnetic field coils 11 apply reference bias magnetic fields in the same direction as an incidence direction of pump light with respect to the sensitivity regions ARa to ARd to the insides of the cells 2. Accordingly, rotation axes of electron spins of alkali metal atoms pumped inside the cells 2 are aligned in the y axis direction. The bias magnetic field coils 15 respectively apply a plurality of bias magnetic fields By having strengths different from each other to the respective sensitivity regions ARa to ARd inside each of the cells 2 in cooperation with the bias magnetic field coils 11. The bias magnetic field coils 15 generate the bias magnetic fields By having different magnetic field strengths in a stepped shape in the four sensitivity regions ARa to ARd inside each of the cells 2. Details of the bias magnetic field coils 15 will be described below. When the magnetic field strengths of bias magnetic fields applied by the bias magnetic field coils 11 and 15 are 14 μT and the alkali metal atoms are potassium, the resonance frequencies of electron spins become 100 kHz. 14 μT is a magnetic field strength which can be easily formed.

The tilting coil 14 generates and radiates an RF signal Rf in order to tilt the rotation axis direction of electron spins of alkali metal atoms pumped inside the cells 2 in a direction perpendicular to the incidence direction of pump light. Specifically, the tilting coil 14 generates the RF signal Rf having the same frequency as the resonance frequencies of electron spins by the bias magnetic field coils 11 (100 kHz when the strengths of the reference bias magnetic fields due to the bias magnetic field coils 11 are 14 μT and the alkali metal atoms are potassium) and radiates the RF signal Rf in the negative z axis direction with a strength and a length required for electron spins to tilt by 90°. In place of the tilting coil 14, a means for radiating different pulsed pump light in a direction orthogonal to the incidence direction of pump light may be provided as an electron spin tilting unit for tilting the direction of electron spins.

The third optical systems 9 each include a total reflection mirror 46, a ½ wavelength plate 47, a polarization beam splitter 48, and a total reflection mirror 49. The total reflection mirror 46 reflects probe light, which has passed through the insides of the cells 2 in the negative z axis direction, in the positive y axis direction. The ½ wavelength plate 47 rotates the polarization plane of probe light reflected by the total reflection mirror 46. This ½ wavelength plate 47 is supported in a manner of being able to rotate about the axis along the y axis such that the rotation angle of the polarization plane of probe light can be adjusted. The polarization beam splitter 48 separates probe light which has been transmitted through the ½ wavelength plate 47 into components of two rays of linear polarized light perpendicular to each other. The component of one ray of linear polarized light is transmitted therethrough in the positive y axis direction and is incident on the optical sensor group 8, and the component of the other ray of linear polarized light is reflected in the positive z direction. The total reflection mirror 49 reflects the component of the other ray of linear polarized light reflected by the polarization beam splitter 48 in the positive y axis direction and causes it to be incident on the optical sensor group 8. Two third optical systems 9 are provided correspondingly to the two cells 2.

The optical sensor group 8 is an element group for detecting polarization plane angles of rays of the probe light QL having passed through the sensitivity regions ARa to ARd and is constituted to include two optical sensor pairs (optical sensors) 43*a* and 43*b* correspondingly to the two respective cells 2. The optical sensor pair 43*a* has two photodiodes 44*a* and 45*a*. The photodiode 44*a* outputs a detection signal indicating the detected strength of the component of the other ray of linear polarized light of the probe light QL, and the photodiode 45*a* outputs a detection signal indicating the detected strength of the component of one ray of linear polarized light of the probe light QL. Similarly, the optical sensor pair 43*b* has two photodiodes.

The read circuit 10 is a processing circuit which is electrically connected to the two optical sensor pairs 43*a* and 43*b* constituting the optical sensor group 8 and performs processing of detection signals output from the two optical sensor pairs 43*a* and 43*b*. That is, the read circuit 10 includes a reading unit for reading detection signals output from the two optical sensor pairs 43*a* and 43*b* (outputs of the optical sensor pairs 43*a* and 43*b*), and a measuring unit for executing processing of measuring external magnetic fields related to the sensitivity regions ARa to ARd based on the detection signals. However, the measuring unit may be constituted to be provided outside the optically pumped magnetometer 1 and execute measurement processing based on a detection signal output from the optically pumped magnetometer 1. The read circuit 10 constitutes a magnetic field measuring unit.

The read circuit 10 is constituted to physically include a memory such as a RAM and a ROM, a processor (arithmetic circuit) such as a CPU, a communication interface, and an auxiliary memory device such as a hard disk and a semiconductor memory. For example, the read circuit 10 may be realized by a personal computer, a cloud server, a smartphone, a tablet terminal, or the like. Functions of the read circuit 10 are realized by the CPU of a computer system executing a program stored in the memory.

Figure 3A:
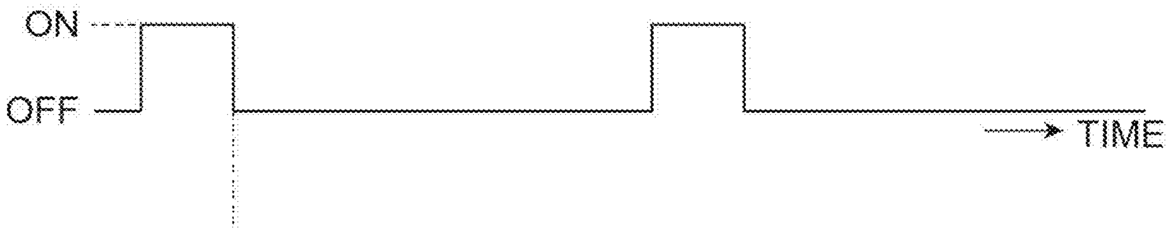
FIG. 3A is timing charts showing generation timings of pump light during processing of measuring an external magnetic field by a read circuit in FIG. 1.
Figure 3B:
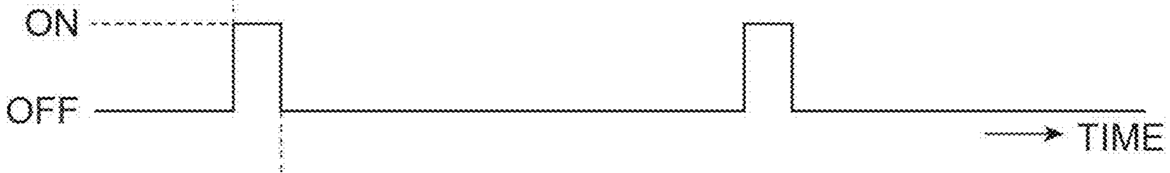
FIG. 3B is timing charts showing generation timings of an RF signal during processing of measuring an external magnetic field by a read circuit in FIG. 1.
Figure 3C:
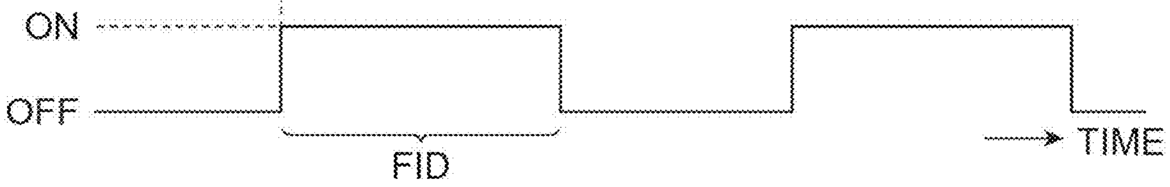
FIG. 3C is timing charts showing generation timings of probe light during processing of measuring an external magnetic field by a read circuit in FIG. 1.
Figure 4:
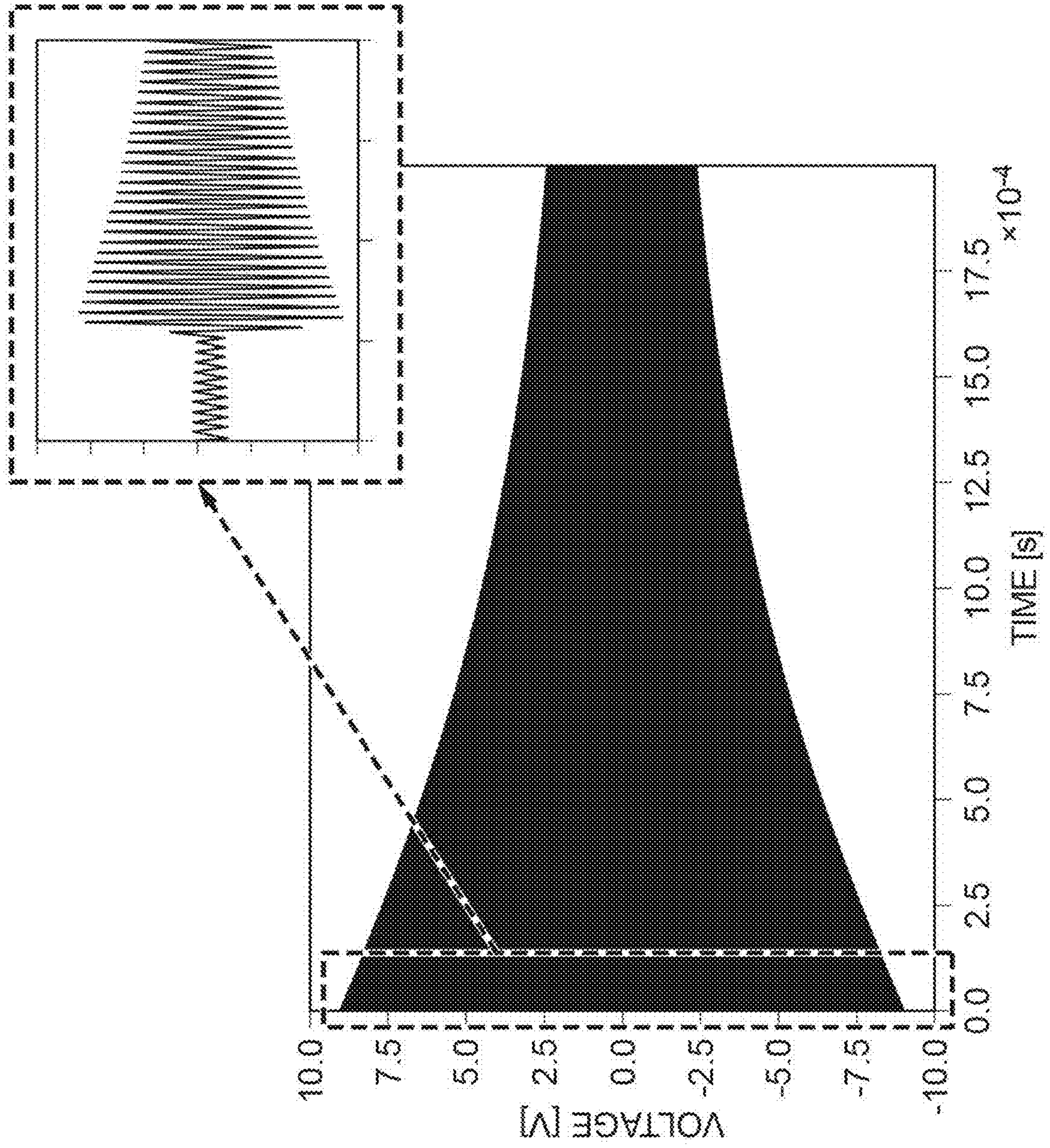
FIG. 4 is a graph showing change over time in FID acquired by the read circuit in FIG. 1.

Functions of processing of measuring an external magnetic field by the measuring unit of the read circuit 10 will be described with reference to FIGS. 3A, 3B, 3C and 4. FIGS. 3A, 3B, 3C show reading timings of pump light, an RF signal, and probe light during processing of measuring an external magnetic field by the read circuit 10. FIG. 3A shows a generation timing of pump light, FIG. 3B shows a generation timing of an RF signal, and FIG. 3C shows a reading timing of probe light. FIG. 4 is a graph showing change over time in free induction decay (FID) acquired by the read circuit 10.

During processing of measuring an external magnetic field by the read circuit 10, pump light is radiated by a control circuit (not illustrated) such that ON and OFF are repeated in a pulsed shape (FIG. 5A), an RF signal is radiated in a pulsed shape immediately after the pump light has shifted from ON to OFF (FIG. 5B), and control is performed such that probe light is read during a predetermined relaxation time after radiation of the RF signal (FIG. 5C). In such a control state, the read circuit 10 acquires detection signals output from the two optical sensor pairs 43*a* and 43*b* during the relaxation time. Further, the read circuit 10 acquires change over time in FID by taking a difference between the detection signals of the two photodiodes 44*a* and 45*a* constituting the optical sensor pair 43*a* (refer to FIG. 4). Similarly, regarding the optical sensor pair 43*b* as well, the read circuit 10 acquires change over time in FID by taking a difference between the detection signals of the two photodiodes.

The waveform of FID acquired in the present embodiment is a mixed waveform including components of first to fourth resonance frequencies corresponding to the sensitivity regions ARa to ARd. Hence, the waveform of FID including the component of a resonance frequency corresponding to the sensitivity region ARa of the mixed waveform of FID will be described as an example, in which FID indicates a situation of relaxation of electron spins of alkali metal atoms and the frequency of precession of electron spins changes in accordance with fluctuation in external magnetic field in the sensitivity region ARa so that the frequency of oscillation changes due to fluctuation in external magnetic field. For example, if the external magnetic field changes from 0 pT to 1 pT while the resonance frequencies of electron spins is 100 kHz, the frequency of precession changes by approximately 0.007 Hz. The read circuit 10 derives a frequency $a_1$ of oscillation of the FID utilizing such characteristics by performing fitting using a function V as shown in the following expression with respect to the waveform of the FID in the initial stage of the relaxation time, and acquires this frequency $a_1$ as a measurement value of the external magnetic field in the sensitivity region ARa. The read circuit 10 can acquire time series data of measurement values by repeating this operation at a frequency of 100 to 1,000 Hz.

$$V = a_0 \sin(2\pi a_1 (t - a_2)) e^{-a_3 t} \quad \text{[Math. 1]}$$

(in the foregoing expression, t indicates time and $a_0$, $a_1$, and $a_2$ indicate predetermined parameters)

Figure 5:
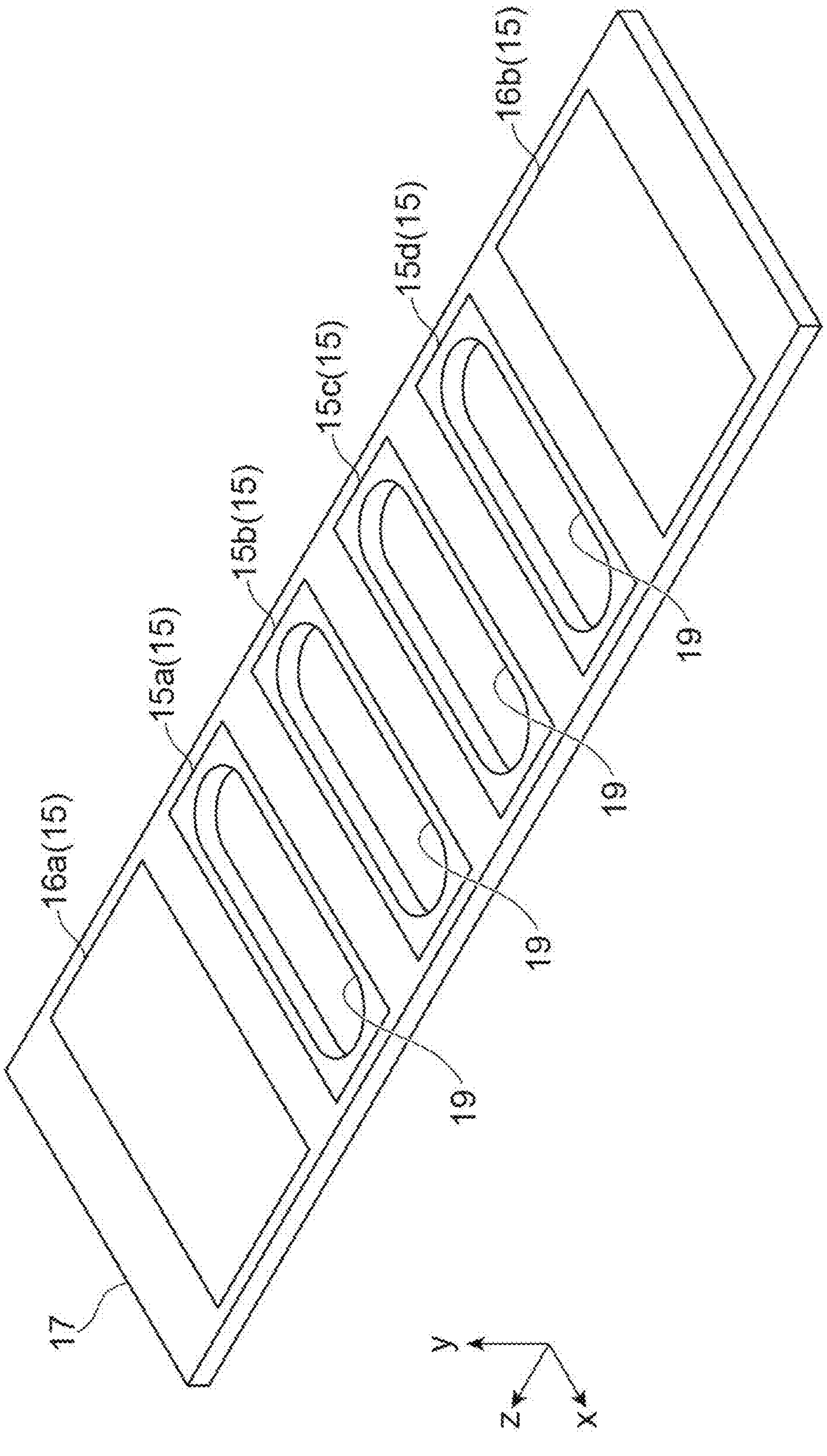
FIG. 5 is a perspective view illustrating bias magnetic field coils in FIG. 1.
Figure 6A:
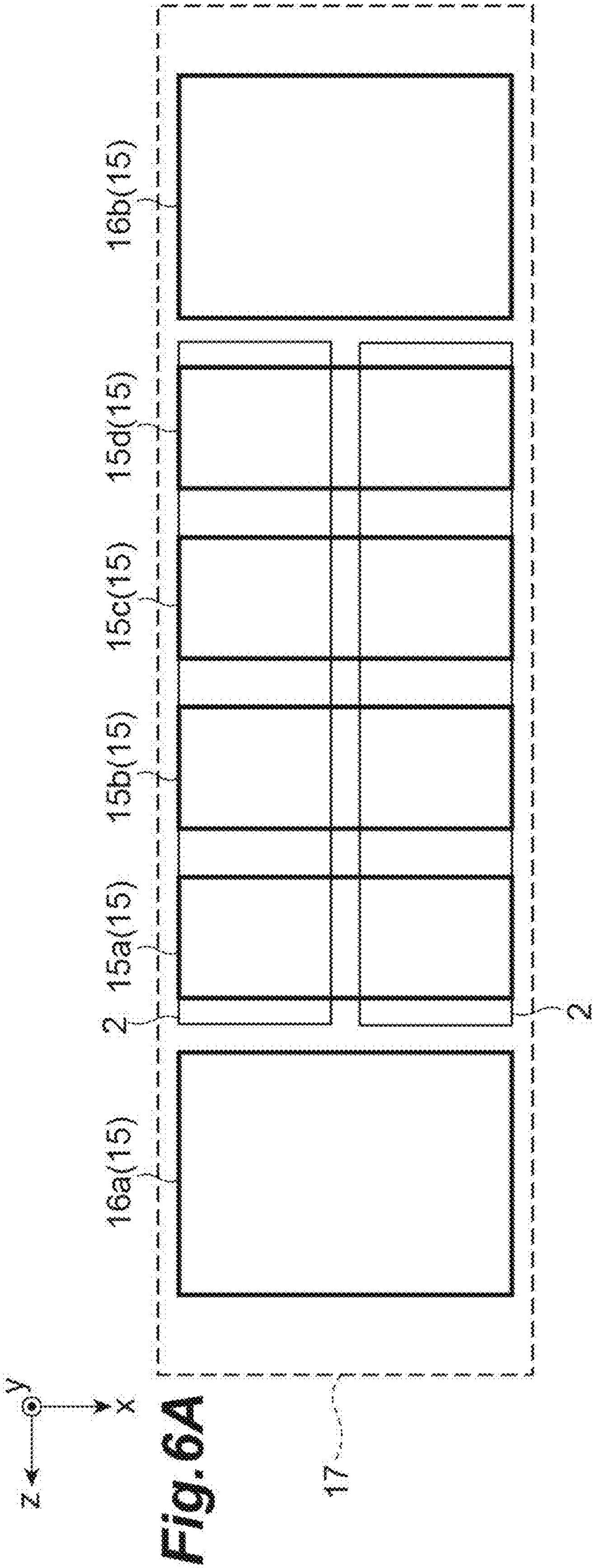
FIG. 6A is a plan view illustrating the bias magnetic field coils in FIG. 1.
Figure 6B:
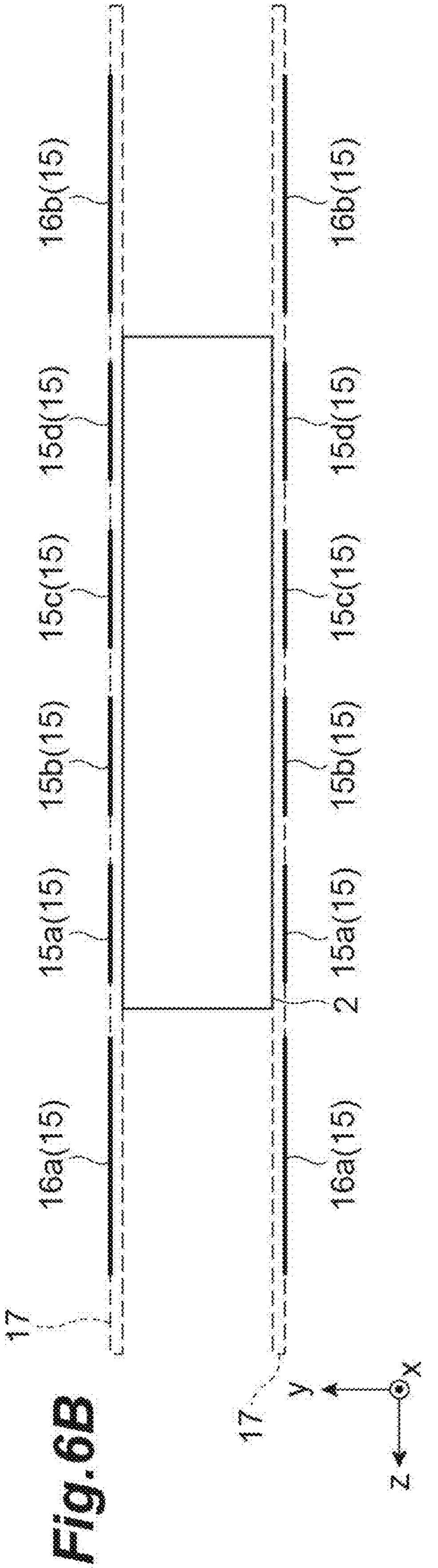
FIG. 6B is a side view illustrating the bias magnetic field coils in FIG. 1.

As illustrated in FIGS. 5 and 6, the bias magnetic field coils 15 each include a first coil 15*a*, a second coil 15*b*, a third coil 15*c*, a fourth coil 15*d*, and extra-cell coils 16*a* and 16*b*. The first coil 15*a* is a coil corresponding to the sensitivity region (first sensitivity region) ARa present in the end portion of each of the cells 2 in the positive z axis direction, and a pair of them are disposed such that the sensitivity region ARa is sandwiched therebetween in the y axis direction. The first coil 15*a* is formed with a first number of windings in one rotation direction (first rotation direction). The first coil 15*a* is provided across the pair of cells 2 when viewed in the y axis direction. The first coil 15*a* is formed such that the sensitivity region ARa of each of the cells 2 is collectively surrounded. The first number of windings is 3, for example.

The second coil 15*b* is a coil corresponding to the sensitivity region (second sensitivity region) ARb of each of the cells 2, and a pair of them are disposed such that the sensitivity region ARb is sandwiched therebetween in the y axis direction. The second coil 15*b* is formed with a second number of windings in one rotation direction. The second coil 15*b* is provided across the pair of cells 2 when viewed in the y axis direction. The second coil 15*b* is formed such that the sensitivity region ARb of each of the cells 2 is collectively surrounded when viewed in the y axis direction. The second number of windings is 1, for example.

The third coil 15*c* is a coil corresponding to the sensitivity region (third sensitivity region) ARc of each of the cells 2, and a pair of them are disposed such that the sensitivity region ARc is sandwiched therebetween in the y axis direction. The third coil 15*c* is formed with the second number of windings in the other rotation direction (second rotation direction) opposite to the one rotation direction. The third coil 15*c* is provided across the pair of cells 2 when viewed in the y axis direction. The third coil 15*c* is formed such that the sensitivity region ARc of each of the cells 2 is collectively surrounded when viewed in the y axis direction.

The fourth coil 15*d* is a coil corresponding to the sensitivity region (fourth sensitivity region) ARd present in the end portion of each of the cells 2 in the negative z axis direction, and a pair of them are disposed such that the sensitivity region ARd is sandwiched therebetween in the y axis direction. The fourth coil 15*d* is formed with the first number of windings in the other rotation direction. The fourth coil 15*d* is provided across the pair of cells 2 when viewed in the y axis direction. The fourth coil 15*d* is formed such that the sensitivity region ARd of each of the cells 2 is collectively surrounded when viewed in the y axis direction.

The extra-cell coils 16*a* are disposed away from the pair of cells 2 in the positive z axis direction when viewed in the y axis direction. A pair of extra-cell coils 16*a* are provided away from each other in the y axis direction. One extra-cell coil 16*a* is positioned adjacent to the first coil 15*a* in the positive z axis direction and at the same position in the y axis direction. The other extra-cell coil 16*a* is positioned adjacent to the other first coil 15*a* in the positive z axis direction and at the same position in the y axis direction. The extra-cell coils 16*b* are disposed away from the pair of cells 2 in the negative z axis direction when viewed in the y axis direction. A pair of extra-cell coils 16*b* are provided away from each other in the y axis direction. One extra-cell coil 16*b* is positioned adjacent to one fourth coil 15*d* in the negative z axis direction and at the same position in the y axis direction. The other extra-cell coil 16*b* is positioned adjacent to the other fourth coil 15*d* in the negative z axis direction and at the same position in the y axis direction.

Figure 7:
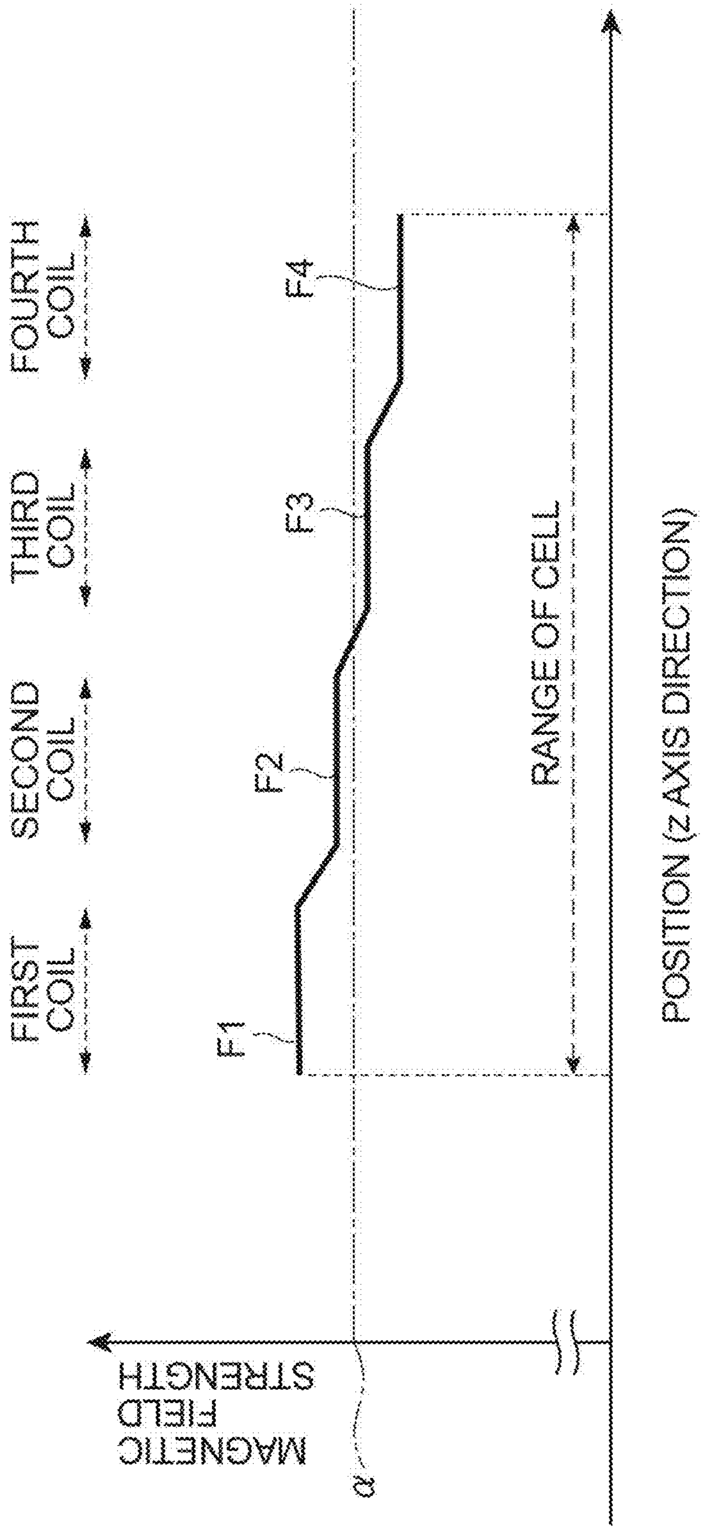
FIG. 7 is a graph showing magnetic field strengths of bias magnetic fields due to the bias magnetic field coils.

As illustrated in FIG. 7, the first to fourth coils 15*a* to 15*d* generate the bias magnetic fields By fluctuating in a stepped shape inside each of the cells 2. The bias magnetic fields By has strength ranges F1 to F4 having strengths different from each other with constant (flat) values at respective z axis positions corresponding to the four sensitivity regions ARa to ARd. The bias magnetic fields By fluctuate in a symmetrically stepped shape based on a reference bias magnetic field α.

For example, by causing a predetermined current to flow in the first to fourth coils 15*a* to 15*d*, regarding the bias magnetic fields By, 0.14 μT is added to the reference bias magnetic field α in the first coil 15*a,* 0.07 μT is added to the reference bias magnetic field α in the second coil 15*b,* 0.07 μT is subtracted from the reference bias magnetic field a in the third coil 15*c*, and 0.14 μT is subtracted from the reference bias magnetic field α in the fourth coil 15*d*. As above, according to the bias magnetic field coils 15, the resonance frequencies of electron spins in the four sensitivity regions ARa to ARd can be set to the first to fourth resonance frequencies different from each other. For example, when the alkali metal atoms are potassium, the first resonance frequency is 98.5 kHz, the second resonance frequency is 99.5 kHz, the third resonance frequency is 100.5 kHz, and the fourth resonance frequency is 101.5 kHz.

As illustrated in FIGS. 5 and 6, substrates 17 are disposed on one side and the other side of each of the cells 2 in the y axis direction. The substrates 17 are printed boards having the y axis direction as a thickness direction. The substrates 17 each have an elongated rectangular shape in the z axis direction. The substrates 17 are disposed across the pair of cells 2 in the x axis direction.

One first coil 15*a*, one second coil 15*b*, one third coil 15*c*, one fourth coil 15*d*, one extra-cell coil 16*a*, and one extra-cell coil 16*b* are provided in the substrate 17 on one side. The other first coil 15*a*, the other second coil 15*b*, the other third coil 15*c*, the other fourth coil 15*d*, the other extra-cell coil 16*a*, and the other extra-cell coil 16*b* are provided in the substrate 17 on the other side.

Passing holes 19 through which pump light passes are formed in the substrates 17. Shapes of the passing holes 19 are track shapes having the x axis direction as the longitudinal direction. Four passing holes 19 are formed correspondingly to the sensitivity regions ARa to ARd. The four passing holes 19 are respectively positioned on inward sides of the first to fourth coils 15*a* to 15*d*. The four passing holes 19 are disposed in a manner of overlapping the sensitivity regions ARa to ARd of each of the cells 2 when viewed in the y axis direction and expose the sensitivity regions ARa to ARd of each of the cells 2. The passing holes 19 need only be formed in the substrate 17 disposed on the incidence surface side or the emission surface side for pump light in the cells 2.

Figure 8:
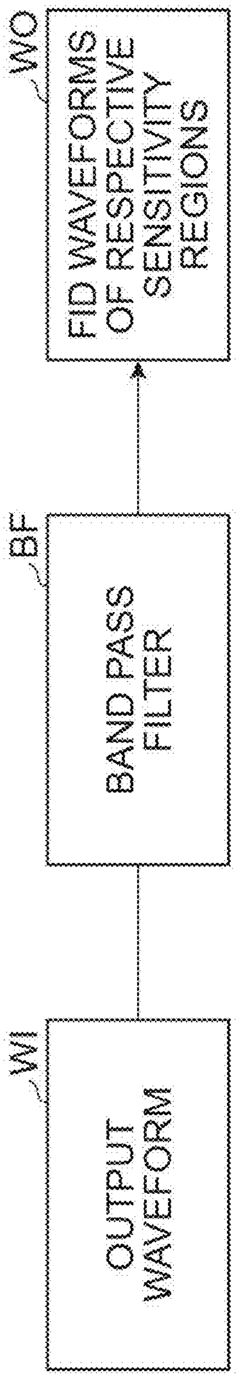
FIG. 8 is a functional block diagram showing processing of the read circuit in FIG. 1.

As described above, the read circuit 10 acquires, as an output waveform, the mixed waveform of FID including the components of the first to fourth resonance frequencies which are the resonance frequencies of electron spins in the sensitivity regions ARa to ARd based on outputs of the optical sensor pairs 43*a* and 43*b*. As illustrated in FIG. 8, the read circuit 10 filters an acquired output waveform WI using a band pass filter BF and acquires waveforms (first to fourth waveforms) WO of FID in the respective bands of the first to fourth resonance frequencies.

Figure 9A:
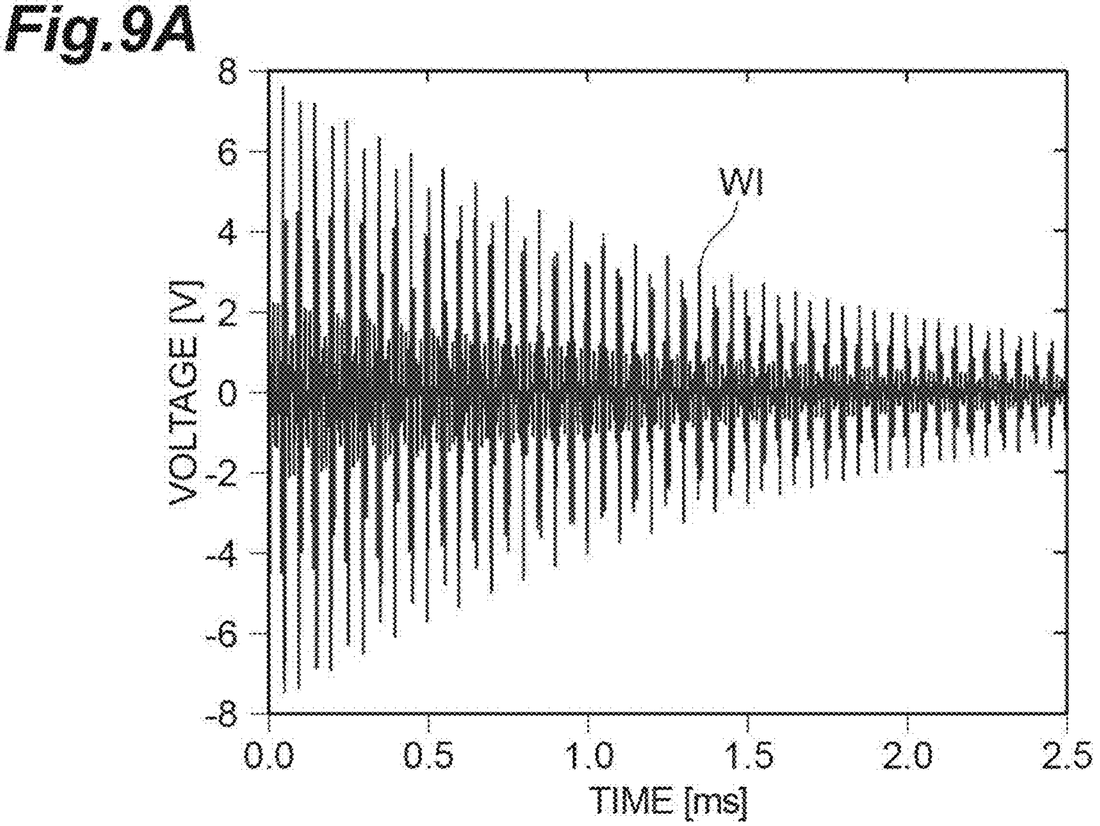
FIG. 9A is a graph showing an output waveform.

As an example, the read circuit 10 acquires the output waveform WI (refer to FIG. 9A) which is a mixed waveform including a plurality of frequency components reflecting the different bias magnetic fields By in the respective sensitivity regions ARa to ARd. The output waveform WI is the sum of the waveforms including the components of the first to fourth resonance frequencies different from each other. The read circuit 10 applies the band pass filter BF having frequency bands (fi±Δf) corresponding to the first to fourth resonance frequencies of the respective sensitivity regions ARa to ARd. Accordingly, the read circuit 10 extracts the waveforms WO of FID (refer to FIG. 9B) in the respective bands of the first to fourth resonance frequencies.

Figure 9B:
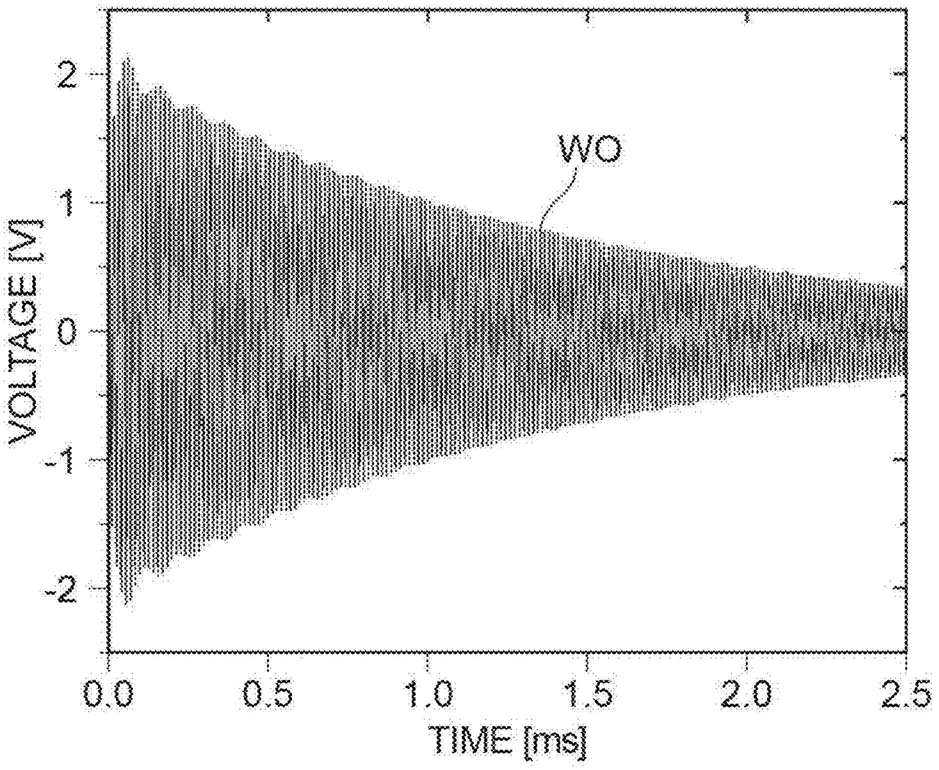
FIG. 9B is a graph showing a waveform of FID in a band of a first resonance frequency.

Further, the read circuit 10 derives the frequency $a_1$ of each of the waveforms WO of FID by performing fitting using the function V with respect to each of the waveforms WO of FID described above. The derived frequency $a_1$ is acquired as a measurement value of an external magnetic field in the sensitivity regions ARa to ARd. The waveform of FID shown in FIG. 9B is that of the band of the first resonance frequency (for example, 98.2 kHz to 98.8 kHz), and the result of fitting indicates the magnetic field strength corresponding to the sensitivity region ARa. For example, if the measured magnetic field is 100 pT or lower, the band width can be sufficiently measured at 0.6 kHz, and there will be no crosstalk with adjacent frequencies.

In the optically pumped magnetometer 1 described above, electron spins of alkali metal atoms are generated (pumped) by emitting pump light to each of the cells 2 filled with alkali metal vapor. Rays of the probe light QL are emitted to the sensitivity regions ARa to ARd inside each of the cells 2, and the polarization plane angles of rays of the probe light QL having passed through the sensitivity regions ARa to ARd are detected by the optical sensor pairs 43*a* and 43*b*. At this time, the bias magnetic fields By fluctuating in a stepped shape are generated inside each of the cells 2 by the bias magnetic field coils 15, and the resonance frequencies of electron spins in the sensitivity regions ARa to ARd become the first to fourth resonance frequencies different from each other.

The output waveform WI which is a mixed waveform of FID including the components of the first to fourth resonance frequencies for each of the cells 2 is acquired by the read circuit 10 based on outputs of the optical sensor pairs 43*a* and 43*b*. The read circuit 10 filters the output waveform WI and acquires the waveforms WO of FID in the respective bands of the first to fourth resonance frequencies. Fitting is performed by the read circuit 10 with respect to each of the waveforms WO of FID using the function V, and the frequency a of each FID is acquired as the measurement value of the magnetic field Bm in the negative y axis direction in the sensitivity regions ARa to ARd.

Hereinabove, in the present embodiment, the strength of the bias magnetic field By can be changed for each of the plurality of sensitivity regions ARa to ARd, and the magnetic field strengths related to the plurality of sensitivity regions ARa to ARd can be obtained using one ray of the probe light QL. That is, multi-channel measurement of magnetic field strengths can be performed with a simple constitution. In other words, multi-channel measurement of the magnetic field Bm can be performed by changing the strength of the bias magnetic field By for each of the plurality of sensitivity regions ARa to ARd using one ray of the probe light QL. The present embodiment, in which the number of rays of the probe light QL is reduced, is important for miniaturization.

In the present embodiment, the bias magnetic field coils 15 include the first to fourth coils 15*a* to 15*d* respectively corresponding to the sensitivity regions ARa to ARd. In this case, change in strength of a bias magnetic field for each of the sensitivity regions ARa to ARd can be specifically realized.

The present embodiment includes the substrates 17 provided with the first to fourth coils 15*a* to 15*d*, and the passing holes 19 through which pump light passes are formed in the substrates 17. In this case, the bias magnetic field coils 15 can be specifically mounted without disturbing incidence of pump light on the cells 2.

In the present embodiment, the bias magnetic field coils 15 include the extra-cell coils 16*a* and 16*b* which are adjacent to the sensitivity regions ARa and ARd present in the end portions of the cells 2 and are disposed away from the cells 2 when viewed in the y axis direction. In this case, the strengths in the bias magnetic fields By on one end side and the other end side of the cells 2 applied to the sensitivity regions ARa and ARd can be appropriately maintained due to the presence of the extra-cell coils 16*a* and 16*b*. Specifically, in the example of the bias magnetic field By shown in FIG. 7, regarding the flat strength range F1 of which the position is present at the farthest negative side in the z axis direction, falling of the negative side thereof in the z axis direction (decreasing and not becoming flat) can be curbed. In addition, regarding the flat strength range F4 of which the position is present at the farthest positive side in the z axis direction, rising of the positive side thereof in the z axis direction (increasing and not becoming flat) can be curbed.

In the present embodiment, the first coil 15*a* is formed with the first number of windings in one rotation direction, the second coil 15*b* is formed with the second number of windings in the one rotation direction, the third coil 15*c* is formed with the second number of windings in the other rotation direction, and the fourth coil 15*d* is formed with the first number of windings in the other rotation direction. In this case, change in strength of a bias magnetic field for each of the sensitivity regions ARa to ARd can be specifically realized. The bias magnetic fields By having different magnetic field strengths in a stepped shape can be realized in the four sensitivity regions ARa to ARd inside the cells 2.

In the present embodiment, the read circuit 10 acquires the output waveform WI which is a mixed waveform of FID including the components of the first to fourth resonance frequencies, filters the output waveform WI using the band pass filter BF, and acquires each of the waveforms WO of FID in the respective bands of the first to fourth resonance frequencies. Further, the read circuit 10 obtains the magnetic field strengths related to the sensitivity regions ARa to ARd on the basis of the frequency of each of the waveforms WO of FID. In this case, the magnetic field strengths related to the sensitivity regions ARa to ARd can be specifically measured.

The present embodiment is provided with the bias magnetic field coils 11 for applying a bias magnetic field in the same direction as pump light and determining the resonance frequencies of electron spins, and the tilting coil 14 for tilting the direction of electron spins in a direction perpendicular to pump light. In this case, the measurement sensitivity of an external magnetic field can be maintained without being influenced by an environmental magnetic field by measuring the strength of the external magnetic field on the basis of the frequency of change in polarization plane angle of probe light detected using detection signals.

In the present embodiment, the tilting coil 14 for radiating the RF signal having the same frequency as the resonance frequency is used. In this case, the rotation axis direction of electron spins can be tilted utilizing the RF signal. Using a simple means, measurement of an external magnetic field based on the frequency of change in polarization plane angle of probe light can be realized. In the present embodiment, a light source radiating pulsed light can also be used. In this case, the rotation axis direction of electron spins can be tilted utilizing pulsed light. Using a simple means, measurement of an external magnetic field based on the frequency of change in polarization plane angle of probe light can be realized.

The present embodiment has the sensitivity regions ARa to ARd divided into four in the z axis direction. For this reason, common mode noise can be removed by acquiring the difference value between the measurement values of the external magnetic fields acquired in two adjacent sensitivity regions of the four divided sensitivity regions ARa to ARd. Namely, in the present embodiment, there are two or more sensitivity regions, and the read circuit 10 can measure the magnetic field strength based on the difference between outputs of the optical sensors corresponding to the two adjacent sensitivity regions. In this case, common mode noise common to the two adjacent sensitivity regions is removed so that measurement of a weak magnetic field strength can be realized and the sensitivity of the magnetic field strength can be further enhanced. The effect of enhancing sensitivity is particularly noticeable when there is no magnetic shield. For example, the detection limit of 20 pT/rHz can be reduced to 300 ft/rHz or lower by approximately two orders of magnitude.

In the present embodiment, it is important to widen the sensitivity regions ARa to ARd in order to improve the sensitivity. In this respect, the inner diameter of the cell 2 is preferably 10×10 mm. At this time, it is preferable that the beam diameter of pump light be 4 mm and the beam diameter of probe light be 3 mm. When four sensitivity regions are provided at intervals of 10 mm, due to the size limitation of the polarization beam splitters 23*a*, 23*b*, and 23*c* for dividing pump light, it is desirable to form pump light into a substantially rectangular shape (for example, 10 mm×4 mm), increase the region intersecting probe light, and limit pump light in a direction orthogonal to it.

Hereinabove, various embodiments of the present disclosure have been described, but the present disclosure is not limited to the foregoing embodiments and may be modified or applied to other forms within a range not changing the gist described in each claim.

Figure 10:
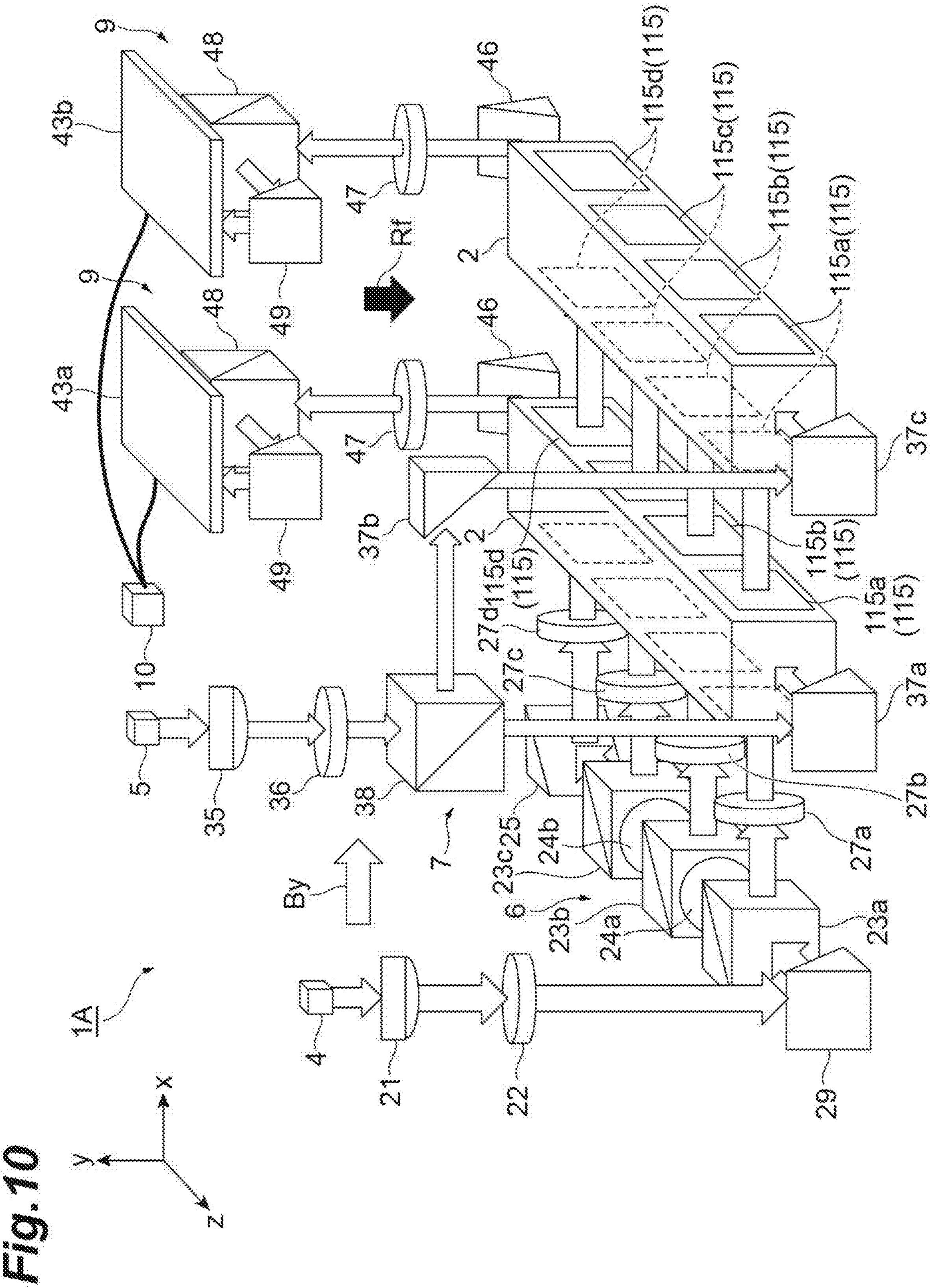
FIG. 10 is a perspective view illustrating a constitution of an optically pumped magnetometer according to a first modification example.

FIG. 10 is a perspective view illustrating a constitution of an optically pumped magnetometer 1A according to a first modification example. The optically pumped magnetometer 1A differs from the optically pumped magnetometer 1 in that the incidence direction of probe light on the cell 2 is the negative z axis direction, the applying direction of the bias magnetic fields By is the positive x axis direction, and the radiation direction of the RF signal Rf is the negative y axis direction. Hereinafter, only the constitutions different from those of the optically pumped magnetometer 1 will be described. In FIG. 10, for the sake of convenience, illustration of the heaters 3, the bias magnetic field coils 11, and the tilting coil 14 is omitted.

The first optical system 6 is constituted to include a total reflection mirror 29. The total reflection mirror 29 reflects pump light which has been transmitted through the ½ wavelength plate 22 in the negative z axis direction and causes it to be incident on the polarization beam splitter 23*a*. The first optical system 6 is constituted such that pump light of four systems transmitted through the four ¼ wavelength plates 27*a*, 27*b*, 27*c*, and 27*d* can be incident in the x axis direction on the sensitivity regions ARa to ARd inside the cell 2.

The optically pumped magnetometer 1A includes bias magnetic field coils 115 in place of the bias magnetic field coils 15 (refer to FIG. 1). The bias magnetic field coils 115 each have a function similar to those of the bias magnetic field coils 15 and generate bias magnetic fields having different magnetic field strengths in a stepped shape in the four sensitivity regions ARa to ARd inside each of the cells 2. The bias magnetic field coils 115 include first to fourth coils 115*a* to 115*d* provided in each of the two cells 2.

The first coil 115*a* is a coil corresponding to the sensitivity region ARa, and a pair of them are disposed such that the sensitivity region ARa is sandwiched therebetween in the x axis direction. The first coil 115*a* is formed to surround the sensitivity region ARa when viewed in the x axis direction. The second coil 115*b* is a coil corresponding to the sensitivity region ARb, and a pair of them are disposed such that the sensitivity region ARb is sandwiched therebetween in the x axis direction. The second coil 115*b* is formed to surround the sensitivity region ARb when viewed in the x axis direction. The third coil 115*c* is a coil corresponding to the sensitivity region ARc, and a pair of them are disposed such that the sensitivity region ARc is sandwiched therebetween in the x axis direction. The third coil 115*c* is formed to surround the sensitivity region ARc when viewed in the x axis direction. The fourth coil 115*d* is a coil corresponding to the sensitivity region ARd, and a pair of them are disposed such that the sensitivity region ARd is sandwiched therebetween in the x axis direction. The fourth coil 115*d* is formed to surround the sensitivity region ARd when viewed in the x axis direction.

In this optically pumped magnetometer 1A as well, regarding the sensitivity regions ARa to ARd, the measurement value of the magnetic field Bm (refer to FIG. 2) in the negative y axis direction can be acquired. This optically pumped magnetometer 1A also exhibits the foregoing operational effect of enabling multi-channel measurement of magnetic field strengths with a simple constitution. In the optically pumped magnetometer 1A, since pump light is radiated across the plurality of cells 2, the plurality of cells 2 can be pumped at the same time. For example, when a multi-channel module constitution such as 4×4 (a constitution in which four sensitivity regions are set in each of the two cells 2) is employed, branching of pump light is minimized to simplify the constitution so that the optically pumped magnetometer 1A can be miniaturized.

Figure 11:
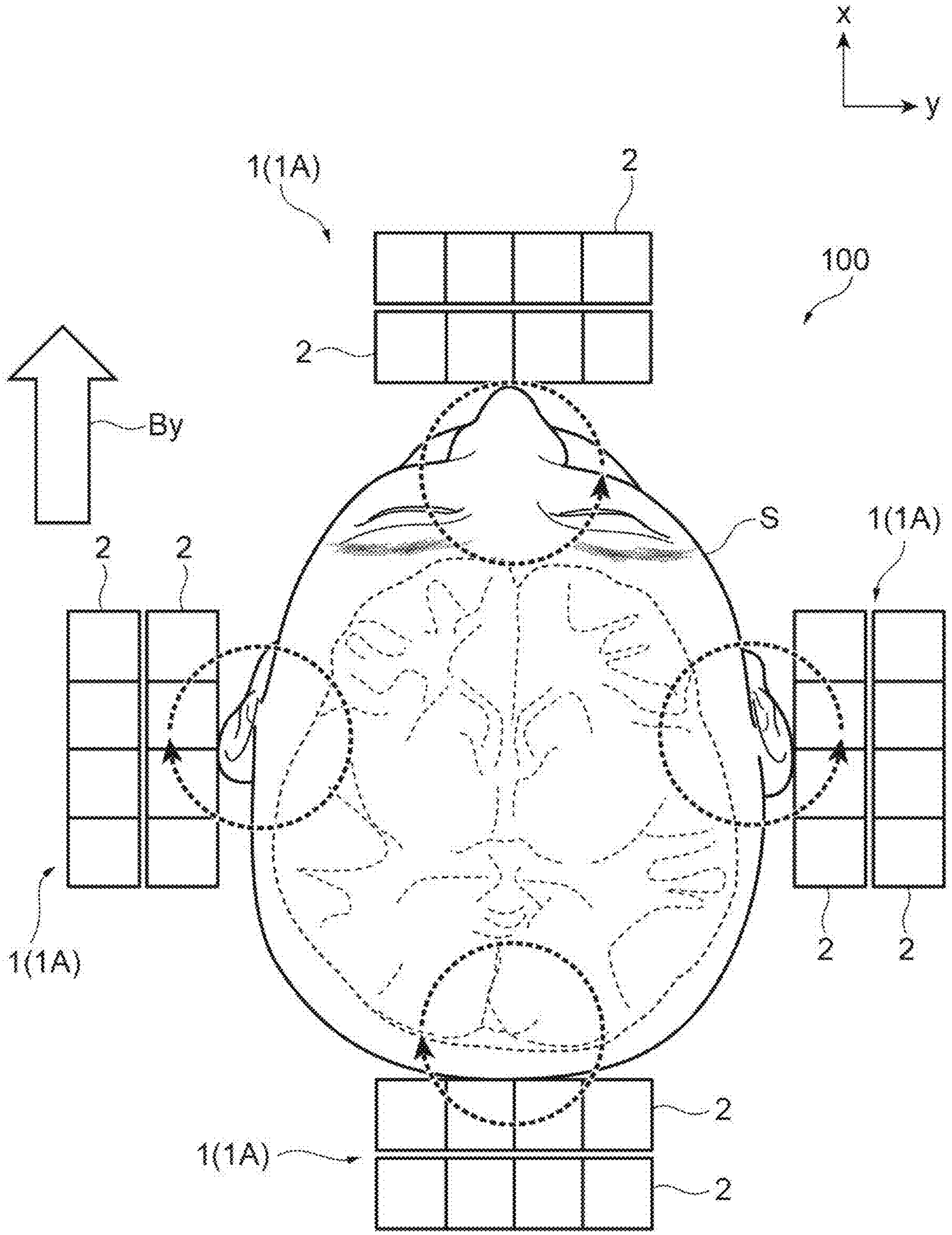
FIG. 11 is a plan view illustrating a constitution of a magnetoencephalograph according to the embodiment.

FIG. 11 is a plan view illustrating a constitution of a magnetoencephalograph 100 according to another embodiment. The magnetoencephalograph 100 includes a plurality of optically pumped magnetometers 1 or optically pumped magnetometers 1A provided in a manner of being able to be disposed around a head (test object) S of a test subject. In the illustrated example, the plurality of optically pumped magnetometers 1 or optically pumped magnetometers 1A provided in the magnetoencephalograph 100 are disposed in a manner of facing each other in the y axis direction with the head S therebetween and are disposed in a manner of facing each other in the x axis direction with the head S therebetween. In the pair of optically pumped magnetometers 1 or optically pumped magnetometers 1A facing each other in the y axis direction, two cells 2 are disposed while having the x axis direction as the longitudinal direction and side by side in the y axis direction. In the pair of optically pumped magnetometers 1 or optically pumped magnetometers 1A facing each other in the x axis direction, two cells 2 are disposed while having the y axis direction as the longitudinal direction and side by side in the x axis direction.

In addition, the bias magnetic field coils 11, bias magnetic field gradient correction coils 12 and 13, and the tilting coil 14 are shared between the plurality of optically pumped magnetometers 1 and the plurality of optically pumped magnetometers 1A. The bias magnetic fields By are applied in the x axis direction through the bias magnetic field coils 11. The optically pumped magnetometers 1 and 1A measure strengths of magnetic fields emitted from the head S.

According to the magnetoencephalograph 100 having the foregoing constitution, measurement values of measured weak magnetic fields from the head S can be acquired. Specifically, according to the disposition example of FIG. 11, measurement values of magnetic fields in the sensitivity regions (8×4=32) in the x axis direction can be acquired. In addition, weak magnetoencephalography having common mode noise removed therefrom can be measured by acquiring a difference between the measurement values of the sensitivity regions closer to the head S and the measurement values of the sensitivity regions adjacent to the sensitivity regions on the outward side of the head S.

The magnetoencephalograph 100 can also be applied to a constitution in which the optically pumped magnetometer 1 and the optically pumped magnetometer 1A are disposed only at positions closer to the head S and are not disposed in parallel. In this case, weak magnetoencephalography having common mode noise removed therefrom can be measured by acquiring a difference between the measurement values of two adjacent sensitivity regions of one optically pumped magnetometer 1 and one optically pumped magnetometer 1A. Since the magnetoencephalograph 100 also includes the optically pumped magnetometers 1 and 1A, the foregoing operational effect of enabling multi-channel measurement of magnetic field strengths with a simple constitution is exhibited.

Figure 12:
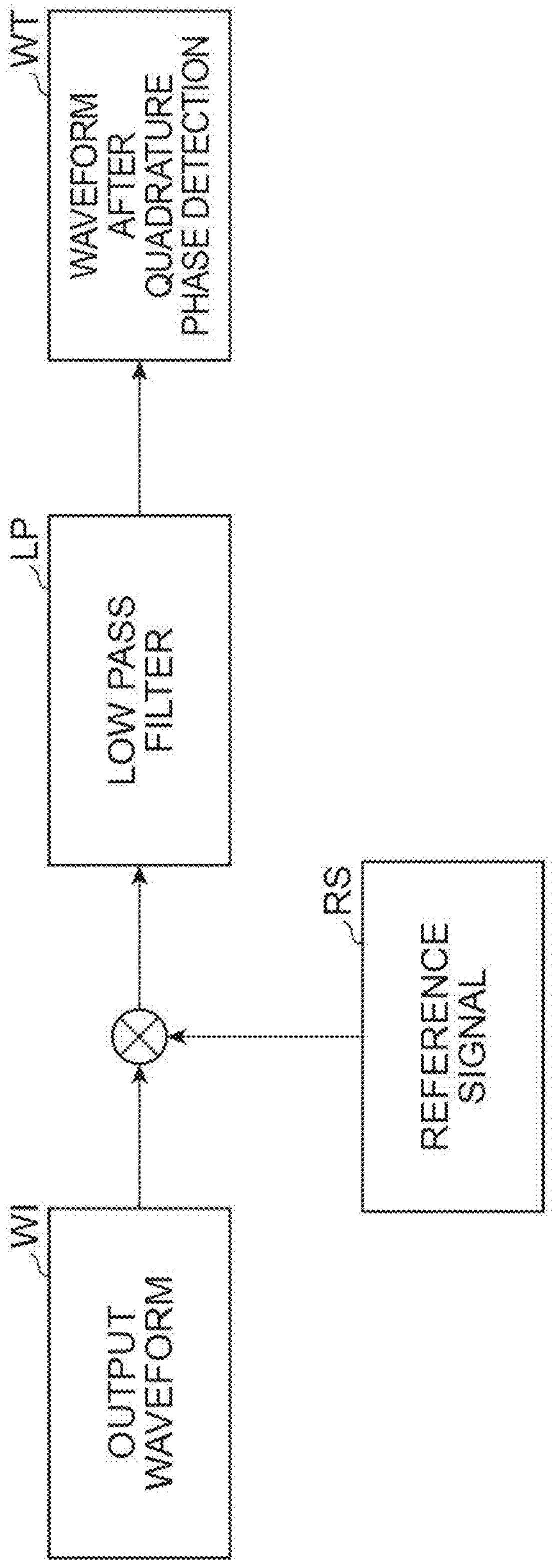
FIG. 12 is a functional block diagram showing processing of the read circuit according to a modification example.

In the foregoing embodiment, the read circuit 10 acquires the waveforms WO of FID in the respective bands of the first to fourth resonance frequencies by filtering the acquired output waveform WI using the band pass filter BF, but the embodiment is not limited to this. For example, the following signal processing procedure using quadrature phase detection may be employed. That is, as illustrated in FIG. 12, the read circuit 10 acquires the output waveform WI which is a mixed waveform including a plurality of frequency components reflecting the different bias magnetic fields By in the respective sensitivity regions ARa to ARd. The read circuit 10 generates a reference signal (a sine wave or a cosine wave having a predetermined frequency) and multiplies it by the output waveform WI. The read circuit 10 applies a low pass filter LF having a cutoff frequency. Accordingly, a waveform WT after quadrature phase detection which is a waveform of FID reflecting the frequency difference with respect to the reference signal is obtained. Fitting is performed with respect to the waveform WT after quadrature phase detection, and the frequency difference with respect to the reference signal in the respective bands of the first to fourth resonance frequencies is obtained.

The foregoing embodiment has the four sensitivity regions ARa to ARd but may be changed to a constitution having two sensitivity regions. In such a case as well, common mode noise can be removed and detection accuracy can be enhanced by acquiring the difference between the measurement values in the two sensitivity regions. In the foregoing embodiment, one, three, five, or more sensitivity regions may be provided. In other words, the plurality of sensitivity regions may include first to Nth sensitivity regions (N is an integer equal to or larger than 2). In this case, the bias magnetic field coils 15 and 115 respectively may apply first to Nth bias magnetic fields to the first to Nth sensitivity regions, and the resonance frequencies of the first to Nth sensitivity regions may be first to Nth resonance frequencies. The read circuit 10 may acquire the mixed waveform of FID including the components of the first to Nth resonance frequencies, filter the acquired mixed waveform of FID, acquire first to Nth waveforms of FID in the respective bands of the first to Nth resonance frequencies, derive respective frequencies of the first to Nth waveforms, and may obtain the magnetic field strengths related to the first to Nth sensitivity regions on the basis of the respectively derived frequencies of the first to Nth waveforms.

The foregoing embodiment is constituted to include two cells 2 but may be constituted to include one, three, or more cells 2. In the foregoing embodiment, one heater 3 may be provided as long as one heater 3 can sufficiently heat two cells 2. In this case, the two cells 2 may be disposed close to each other. For example, the interval between the two cells 2 may be 15 mm.

In the foregoing embodiment, it is preferable that the bias magnetic fields By have a smaller gradient in the x axis direction and the z axis direction in order to realize higher sensitivity. Hence, for example, the gradient of the bias magnetic fields By may be corrected and the uniformity of the bias magnetic fields By may be enhanced by providing a bias magnetic field gradient correction coil such as a parallel four-wire coil. At this time, the bias magnetic field gradient correction coil may correct the gradient such that the relaxation times of FID in the respective bands of the first to fourth resonance frequencies become longer. In the foregoing embodiment, there have been cases where light of linear polarized light is used by being converted into light of circularly polarized light, but light of circularly polarized light may be used from the beginning without performing the conversion.

According to the present disclosure, it is possible to provide an optically pumped magnetometer and a magnetoencephalograph enabling multi-channel measurement of magnetic field strengths with a simple constitution.

What is claimed is:

1. An optically pumped magnetometer comprising:

a cell configured to be filled with alkali metal vapor;

a pump light incidence unit including a pump laser, configured to cause pump light for pumping alkali metal atoms constituting the alkali metal vapor to be incident on a plurality of sensitivity regions inside the cell in a first direction;

a probe light incidence unit including a probe laser, configured to cause probe light for detecting change in electron spins in a pumped state of the alkali metal atoms to be incident on the plurality of sensitivity regions in a direction intersecting the first direction;

bias magnetic field coils configured to apply a bias magnetic field in the first direction to the inside of the cell and determine a resonance frequency of the electron spins;

an electron spin tilting unit including a tilting coil, configured to tilt a rotation axis direction of the electron spins in a direction perpendicular to the first direction;

an optical sensor configured to detect the probe light having passed through the sensitivity regions;

a magnetic field measuring unit configured to measure magnetic field strengths related to the sensitivity regions based on an output of the optical sensor, wherein the bias magnetic field coils respectively apply a plurality of the bias magnetic fields having strengths different from each other to the plurality of corresponding sensitivity regions, the plurality of sensitivity regions include at least a first sensitivity region and a second sensitivity region, and the bias magnetic field coils include a first coil corresponding to the first sensitivity region, and a second coil corresponding to the second sensitivity region; and a substrate configured to be provided with the first coil and the second coil, wherein a passing hole allowing the pump light to pass therethrough is formed in the substrate.

2. The optically pumped magnetometer according to claim 1, wherein the electron spin tilting unit radiates RF signals having the same frequencies as the resonance frequencies.

3. The optically pumped magnetometer according to claim 1, wherein the electron spin tilting unit radiates pulsed light.

4. The optically pumped magnetometer according to claim 1, wherein the magnetic field measuring unit measures the magnetic field strengths based on a difference between outputs of the optical sensor corresponding to the two adjacent sensitivity regions.

5. A magnetoencephalograph comprising:

the optically pumped magnetometer according to claim 1 configured to be provided in a manner of being able to be disposed around the head of a test object and measure a strength of a magnetic field emitted from the test object.

6. An optically pumped magnetometer comprising:

a cell configured to be filled with alkali metal vapor;

a pump light incidence unit including a pump laser, configured to cause pump light for pumping alkali metal atoms constituting the alkali metal vapor to be incident on a plurality of sensitivity regions inside the cell in a first direction;

a probe light incidence unit including a probe laser, configured to cause probe light for detecting change in electron spins in a pumped state of the alkali metal atoms to be incident on the plurality of sensitivity regions in a direction intersecting the first direction;

bias magnetic field coils configured to apply a bias magnetic field in the first direction to the inside of the cell and determine a resonance frequency of the electron spins;

an electron spin tilting unit including a tilting coil, configured to tilt a rotation axis direction of the electron spins in a direction perpendicular to the first direction;

an optical sensor configured to detect the probe light having passed through the sensitivity regions; and a magnetic field measuring unit configured to measure magnetic field strengths related to the sensitivity regions based on an output of the optical sensor, wherein the bias magnetic field coils respectively apply a plurality of the bias magnetic fields having strengths different from each other to the plurality of corresponding sensitivity regions, the plurality of sensitivity regions include at least a first sensitivity region and a second sensitivity region, the bias magnetic field coils include a first coil corresponding to the first sensitivity region, and a second coil corresponding to the second sensitivity region, the first sensitivity region is present in an end portion of the cell, and the bias magnetic field coils include an extra-cell coil disposed away from the cell when viewed in the first direction and adjacent to the first coil.

7. An optically pumped magnetometer comprising:

a cell configured to be filled with alkali metal vapor;

a pump light incidence unit including a pump laser, configured to cause pump light for pumping alkali metal atoms constituting the alkali metal vapor to be incident on a plurality of sensitivity regions inside the cell in a first direction;

a probe light incidence unit including a probe laser, configured to cause probe light for detecting change in electron spins in a pumped state of the alkali metal atoms to be incident on the plurality of sensitivity regions in a direction intersecting the first direction;

bias magnetic field coils configured to apply a bias magnetic field in the first direction to the inside of the cell and determine a resonance frequency of the electron spins;

an electron spin tilting unit including a tilting coil, configured to tilt a rotation axis direction of the electron spins in a direction perpendicular to the first direction;

an optical sensor configured to detect the probe light having passed through the sensitivity regions; and a magnetic field measuring unit configured to measure magnetic field strengths related to the sensitivity regions based on an output of the optical sensor, wherein the bias magnetic field coils respectively apply a plurality of the bias magnetic fields having strengths different from each other to the plurality of corresponding sensitivity regions, the plurality of sensitivity regions include a first sensitivity region, a second sensitivity region adjacent to the first sensitivity region, a third sensitivity region adjacent to the second sensitivity region, and a fourth sensitivity region adjacent to the third sensitivity region, and the bias magnetic field coils include a pair of first coils disposed with the first sensitivity region sandwiched therebetween in the first direction and formed with a first number of windings in a first rotation direction, a pair of second coils disposed with the second sensitivity region sandwiched therebetween in the first direction and formed with a second number of windings in the first rotation direction, a pair of third coils disposed with the third sensitivity region sandwiched therebetween in the first direction and formed with the second number of windings in a second rotation direction opposite to the first rotation direction, and a pair of fourth coils disposed with the fourth sensitivity region sandwiched therebetween in the first direction and formed with the first number of windings in the second rotation direction.

8. An optically pumped magnetometer comprising:

a cell configured to be filled with alkali metal vapor;

a pump light incidence unit including a pump laser, configured to cause pump light for pumping alkali metal atoms constituting the alkali metal vapor to be incident on a plurality of sensitivity regions inside the cell in a first direction;

a probe light incidence unit including a probe laser, configured to cause probe light for detecting change in electron spins in a pumped state of the alkali metal atoms to be incident on the plurality of sensitivity regions in a direction intersecting the first direction;

bias magnetic field coils configured to apply a bias magnetic field in the first direction to the inside of the cell and determine a resonance frequency of the electron spins;

an electron spin tilting unit including a tilting coil, configured to tilt a rotation axis direction of the electron spins in a direction perpendicular to the first direction;

an optical sensor configured to detect the probe light having passed through the sensitivity regions; and a magnetic field measuring unit configured to measure magnetic field strengths related to the sensitivity regions based on an output of the optical sensor, wherein the bias magnetic field coils respectively apply a plurality of the bias magnetic fields having strengths different from each other to the plurality of corresponding sensitivity regions, the plurality of sensitivity regions include first to Nth sensitivity regions (Nis an integer equal to or larger than 2), the bias magnetic field coils respectively apply first to Nth bias magnetic fields to the first to Nth sensitivity regions and have first to Nth resonance frequencies as the resonance frequencies of the first to Nth sensitivity regions, and the magnetic field measuring unit acquires a mixed waveform of free induction decay including components of the first to Nth resonance frequencies based on an output of the optical sensor, filters the mixed waveform through a band pass filter, acquires first to Nth waveforms of free induction decay in respective bands of the first to Nth resonance frequencies, derives respective frequencies of the first to Nth waveforms, and obtains magnetic field strengths related to the first to Nth sensitivity regions on the basis of the respectively derived frequencies of the first to Nth waveforms.

* * * * *